(12) United States Patent
D'Alessio et al.

(10) Patent No.: US 6,616,019 B2
(45) Date of Patent: Sep. 9, 2003

(54) ADHESIVE APPLICATOR WITH IMPROVED APPLICATOR TIP

(75) Inventors: Keith R. D'Alessio, Cary, NC (US); Michael F. Brady, Cary, NC (US); Anthony S. Voiers, Raleigh, NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 09/906,806

(22) Filed: Jul. 18, 2001

(65) Prior Publication Data

US 2003/0015557 A1 Jan. 23, 2003

(51) Int. Cl.$^7$ .............................................. B43M 11/06
(52) U.S. Cl. ..................... 222/566; 222/547; 604/310; 401/196; 401/132; 401/205
(58) Field of Search ................................ 222/544, 545, 222/547, 562, 566; 604/310; 401/132, 133, 196, 205

(56) References Cited

U.S. PATENT DOCUMENTS

| | | | |
|---|---|---|---|
| 2,439,081 A | | 4/1948 | Dickey et al. |
| 2,768,109 A | | 10/1956 | Coover, Jr. |
| 2,784,127 A | | 3/1957 | Joyner et al. |
| 2,836,333 A | * | 5/1958 | Woodel |
| 2,987,223 A | * | 6/1961 | Armour |
| 3,178,379 A | | 4/1965 | Wicker, Jr. et al. |

(List continued on next page.)

FOREIGN PATENT DOCUMENTS

| | | |
|---|---|---|
| EP | 0 170 526 A2 | 2/1986 |
| EP | 0 463 658 A1 | 1/1992 |
| EP | 0 495 357 A1 | 7/1992 |
| GB | 2 083 743 A | 3/1982 |
| JP | 2-135479 U | 11/1990 |
| WO | WO 91/09641 | 7/1991 |
| WO | WO 96/40797 | 12/1996 |

OTHER PUBLICATIONS

U.S. patent application Ser. No. 09/506,255, Leung, filed Feb. 17, 2000.
U.S. patent application Ser. No. 09/409,672, Leung, filed Sep. 30, 1999.
U.S. patent application Ser. No. 08/909,845, Clark et al., filed Aug. 12, 1997.
U.S. patent application Ser. No. 08/920,876, Clark et al., filed Aug. 29, 1997.
U.S. patent application Ser. No. 09/479,060, Voiers et al., filed Jan. 7, 2000.
U.S. patent application Ser. No. 09/479,059, Clark et al., filed Jan. 7, 2000.
Locite Product No. 11067–2 (Rearview Mirror Adhesive); Jan. 1999.
Permatex Product No. ATA–1 (Auto Trim Adhesive); Jan. 1999.
Instruction Sheet for Immuno AG product TISSEEL KIT VH, Feb. 1993.
Product Literature for MedLogic product LIQUIDRAPE, 1998.

*Primary Examiner*—J. Casimer Jacyna
(74) *Attorney, Agent, or Firm*—Oliff & Berridge, PLC

(57) ABSTRACT

An applicator for dispensing adhesive material, includes a container body, and an applicator tip, where the adhesive material is located in the container body in a non-contacting relationship with the applicator tip prior to dispensing said adhesive material. The applicator tip has a proximal open end open toward said container body for attachment to the container body, a distal end having at least one orifice, a restrictive flow portion located between the proximal end and the distal end, and a flow reducing portion located between the restrictive flow portion and the distal end. The applicator tip defines a fluid flow channel from the proximal end to the distal end and through the restrictive flow portion and the flow reducing portion, where the applicator tip permits the adhesive material to pass through the applicator tip and exit the applicator tip at the at least one orifice.

29 Claims, 10 Drawing Sheets

U.S. PATENT DOCUMENTS

| | | |
|---|---|---|
| 3,223,083 A | 12/1965 | Cobey |
| 3,260,637 A | 7/1966 | von Bramer |
| 3,468,458 A | 9/1969 | Leigh |
| 3,527,841 A | 9/1970 | Wicker, Jr. et al. |
| 3,559,652 A | 2/1971 | Banitt et al. |
| 3,722,599 A | 3/1973 | Robertson et al. |
| 3,728,375 A | 4/1973 | Coover, Jr. et al. |
| 3,759,264 A | 9/1973 | Coover, Jr. et al. |
| 3,770,523 A | 11/1973 | Biswas |
| 3,891,125 A | 6/1975 | Morane et al. |
| 3,922,100 A | 11/1975 | Saito |
| 3,940,362 A | 2/1976 | Overhults |
| 3,964,643 A | 6/1976 | Morane et al. |
| 3,970,505 A | 7/1976 | Hauser et al. |
| 3,995,641 A | 12/1976 | Kronenthal et al. |
| 4,042,442 A | 8/1977 | Dombroski et al. |
| 4,291,131 A | 9/1981 | McIntire et al. |
| 4,297,160 A | 10/1981 | Kusayama et al. |
| 4,340,708 A | 7/1982 | Gruber |
| 4,364,876 A | 12/1982 | Kimura et al. |
| 4,401,272 A * | 8/1983 | Merton et al. |
| 4,408,699 A | 10/1983 | Stock |
| 4,777,230 A | 10/1988 | Kamath |
| 4,783,515 A | 11/1988 | Waniczek et al. |
| 4,801,008 A | 1/1989 | Rich |
| 4,804,691 A | 2/1989 | English et al. |
| 4,921,137 A * | 5/1990 | Heijenga |
| 5,029,738 A | 7/1991 | Dillon |
| 5,059,657 A | 10/1991 | Druliner et al. |
| 5,106,221 A | 4/1992 | Diot et al. |
| 5,199,808 A | 4/1993 | Gueret |
| 5,216,096 A | 6/1993 | Hattori et al. |
| 5,219,328 A | 6/1993 | Morse et al. |
| 5,230,579 A | 7/1993 | Klawson et al. |
| 5,259,835 A | 11/1993 | Clark et al. |
| 5,262,200 A | 11/1993 | Puder et al. |
| 5,328,687 A * | 7/1994 | Leung et al. |
| 5,333,755 A | 8/1994 | Wang et al. |
| 5,445,462 A | 8/1995 | Johnson et al. |
| 5,514,371 A | 5/1996 | Leung et al. |
| 5,514,372 A | 5/1996 | Leung et al. |
| 5,575,997 A | 11/1996 | Leung et al. |
| 5,582,834 A | 12/1996 | Leung et al. |
| 5,624,669 A | 4/1997 | Leung et al. |
| 5,749,498 A * | 5/1998 | Lavoie et al. |
| 5,816,804 A | 10/1998 | Fischer |
| 5,928,611 A | 7/1999 | Leung |
| 5,934,522 A | 8/1999 | Canela et al. |
| 5,981,621 A | 11/1999 | Clark et al. |
| 6,083,002 A * | 7/2000 | Martin et al. |
| 6,099,807 A | 8/2000 | Leung |
| 6,143,805 A * | 11/2000 | Hickey et al. |
| 6,155,265 A | 12/2000 | Hammerslag |
| 6,241,124 B1 * | 6/2001 | Hoyt |
| 6,394,982 B1 * | 5/2002 | Ehrenfels |
| 6,422,777 B1 * | 7/2002 | Landrau et al. |

* cited by examiner

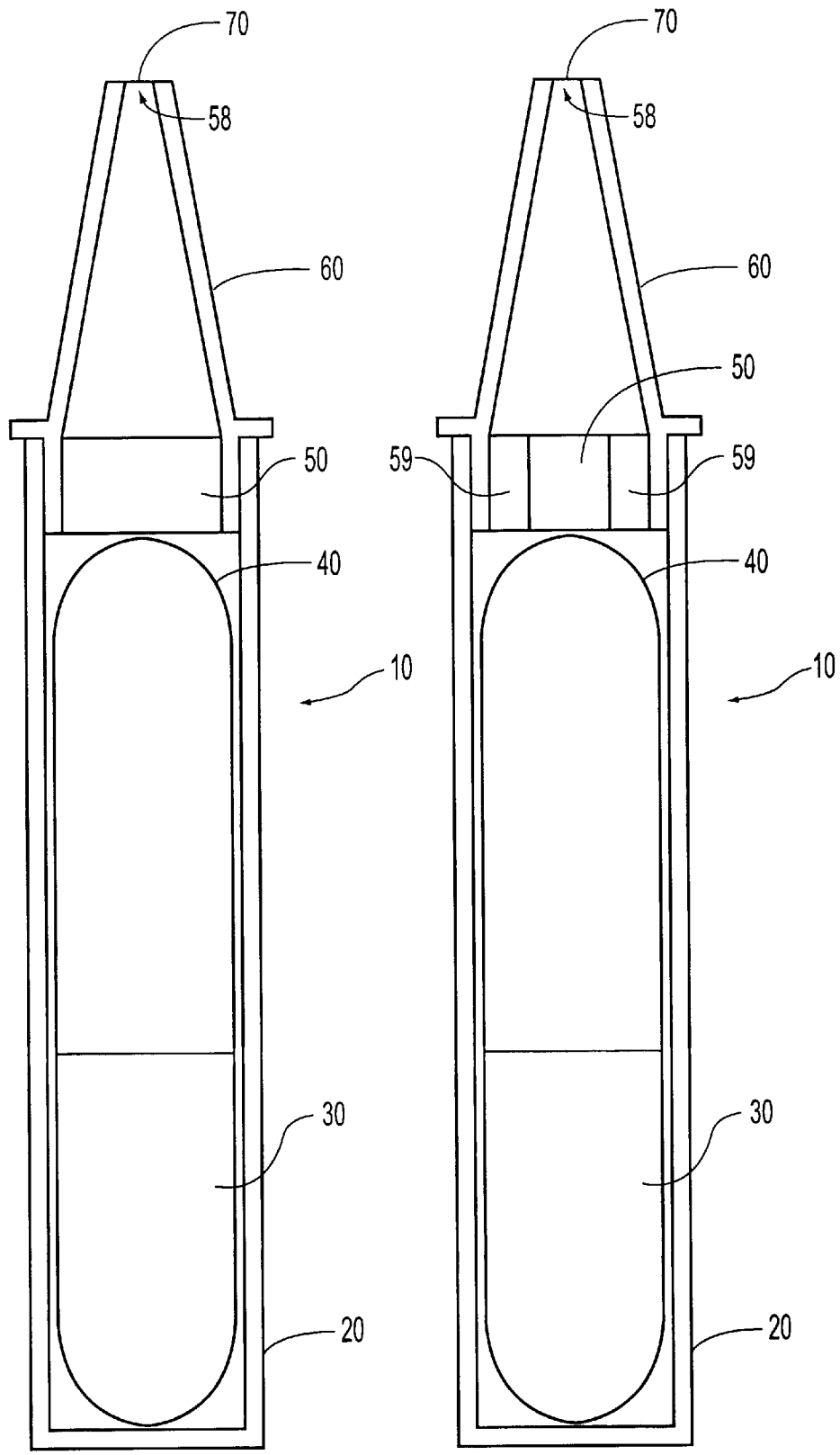

ADHESIVE APPLICATOR WITH IMPROVED APPLICATOR TIP

BACKGROUND OF THE INVENTION

1. Field of Invention

This invention relates to an adhesive applicator with a new and improved applicator tip design.

2. Description of Related Art

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal (including human) tissue. Monomers of α-cyanoacrylates are anionically polymerizable or free radical polymerizable, or polymerizable by zwitterions or ion pairs to form polymers. Once polymerization has been initiated, the cure rate can be very rapid.

Medical applications of adhesive compositions include use as an alternate-or an adjunct to surgical sutures and staples in wound closure as well as for covering and protecting surface wounds such as lacerations, abrasions, burns, ulcers such as stomatitis, sores, and other open surface wounds. When such an adhesive is applied, it is usually applied in its monomeric form, and the resultant polymerization gives rise to the desired adhesive bond.

However, with the application of adhesive in a monomeric form, due to the rapid polymerization rate of the monomers, it has been challenging to design effective and commercially viable packaging and dispensing systems. Such packaging and dispensing systems must counterbalance the competing requirements that the monomer not prematurely polymerize, that the monomer be easily applied, that the monomer polymerize at a desired rate upon application, and that the sanitary and/or sterile properties of the monomer and applicator—whether real or perceived—be maintained.

Various dispensing and packaging systems for adhesives have been proposed. These systems include large bottles with a single applicator, such as a large single- or multi-use brush; small applicators such as small ampoules containing monomer that can be expelled through an integral or replaceable applicator; and the like.

A disadvantage of some known applicator systems, and particularly applicators containing a frangible vial and a porous applicator tip for expelling the adhesive, is that the monomer material is expelled through the entire surface area of the tip, and even to greater extents in areas other than the area used to apply the monomer to the desired substrate. For example, large amounts of adhesive are expelled from areas around the periphery of the applicator tip, where the applicator tip meets the applicator housing, rather than through the end of the applicator tip, as is often desired. This leads to a further problem of less precise control over the area of application of the monomer to the substrate.

For example, an effective applicator system is disclosed in U.S. Pat. No. 5,928,611 to Leung. This patent discloses an applicator system generally comprising a tube containing a frangible vial of monomeric adhesive composition. One end of the tube is sealed, and the other end is closed by an applicator tip comprising a solid support having a polymerization or cross-linking accelerator or initiator for the monomeric adhesive disposed thereon or therein. As shown in FIG. 3 of the patent, the applicator tip can be generally dome shaped. The applicator device of U.S. Pat. No. 5,928,611 is shown as FIG. 1 herein. An applicator device 100 comprises a cylindrical applicator container 200 holding polymerizable and/or cross-linkable material 300 enclosed in a frangible vial 400, and an applicator tip 500 containing a polymerization and/or cross-linking initiator.

However, a difficulty encountered with such a dome-shaped applicator tip, as well as with other solid applicator tips, is that the monomeric adhesive material being expelled through the applicator tip tends to follow paths of least resistance within the tip. That is, as the monomeric adhesive is being expelled, it tends to follow the shortest paths through the tip, which tend to be around the periphery of the tip, rather than following the longer path through the full length of the tip to the end of the tip. Because the end of the tip is desired to be used to apply the adhesive, less precise control of placement of the adhesive is obtained because adhesive is expelled through the entire surface of the tip. This also tends to result in waste of adhesive material, because all of the adhesive does not exit from the tip at the desired location.

A related problem with such applicator tips is that it is difficult to obtain precise placement of the adhesive materials in some uses. For example, it is often difficult to precisely apply the adhesive material in confined spaces, where it is difficult to fit the entire applicator device. Likewise, it is difficult to apply fine lines of the adhesive from such a dome-shaped applicator tip. In such medical procedures as face lifts or intricate surgery, for example, high precision is necessary.

Applicator devices used for Loctite Product No. 11067-2 and Permatex Product No. ATA-1 contain crushable glass ampoules within flexible applicators. However, the compositions within the crushable ampoules are, in both products, adhesive activators, not the adhesive composition itself. In both of these products, the adhesive is contained in a separate dispenser. The dispenser system used for these products is physically similar to that shown in FIG. 1, except that the applicator tip is rectangular in shape, rather than dome-shaped, and the applicator tip does not contain a polymerization and/or cross-linking initiator for an adhesive material contained in the frangible vial. In this product also, the above-described problems of wasted material (here, activator) and less precision in application are also present.

EP 0 170 526 discloses an applicator device for storing and dispensing a two-component product, such as a two-component adhesive. The applicator includes an inner sealed frangible ampoule containing a curable material, an outer flexible sleeve containing the ampoule, with a dispensing nozzle at one end and being sealed at the other end, and a fibrous material impregnated with accelerant. The fibrous material is positioned at least partly around the ampoule at the orifice end of the container between the ampoule and a nozzle.

Accordingly, a need exists in the art for adhesive applicators that will allow more precise placement of the adhesive material. A need also exists in the art for a means to decrease waste of monomeric adhesive material. Still further, a need exists in the art for different types of applicator tip designs, to allow a broader range of use of the adhesive materials.

SUMMARY OF THE INVENTION

The present invention addresses the above and other needs by providing applicator tips that allow increased precision in control of placement of the adhesive composition, and a decrease in waste of adhesive. Applicator tips of embodiments of the present invention can direct the adhesive material that is being expelled from the applicator to a specific desired point, while maintaining control over the flow of the adhesive material.

A benefit provided by the present invention is thus the ability to apply adhesive material in precise patterns, such as in thin lines, which was either more difficult or not possible using prior applicator systems. The present invention also allows tailoring of the application pattern based on alternative designs of the applicator tip, thus allowing flexibility in application of, for example, from thin lines to thicker lines. The present invention also permits decreased waste of adhesive material, by allowing effective use of a greater portion of the volume of adhesive material contained within the applicator.

In embodiments, the present invention provides an applicator for dispensing adhesive material, comprising:

a container body, and an applicator tip, wherein said adhesive material is located in said container body in a non-contacting relationship with said applicator tip prior to dispensing said adhesive material, said applicator tip having a proximal open end open toward said container body for attachment to said container body, a distal end having at least one orifice, a restrictive flow portion located between said proximal end and said distal end, and a flow reducing portion located between said restrictive flow portion and said distal end, said applicator tip defining a fluid flow channel from said proximal end to said distal end and through said restrictive flow portion and said flow reducing portion, wherein said applicator tip permits said adhesive material to pass through said applicator tip and exit said applicator tip at said at least one orifice.

In embodiments, the present invention provides a kit for dispensing adhesive material, comprising at least one saleable package containing: at least one applicator comprising a container body and an adhesive material located in the container body, and at least two applicator tips that are attachable to the applicator and have different configurations, wherein said kit contains more applicator tips than applicators.

BRIEF DESCRIPTION OF THE DRAWINGS

These and other advantages and features of this invention will be apparent from the following, especially when considered with the accompanying drawings, in which:

FIGS. 2a–2d are side elevational views of comparative applicator devices;

DETAILED DESCRIPTION OF PREFERRED EMBODIMENTS

Figure 1:
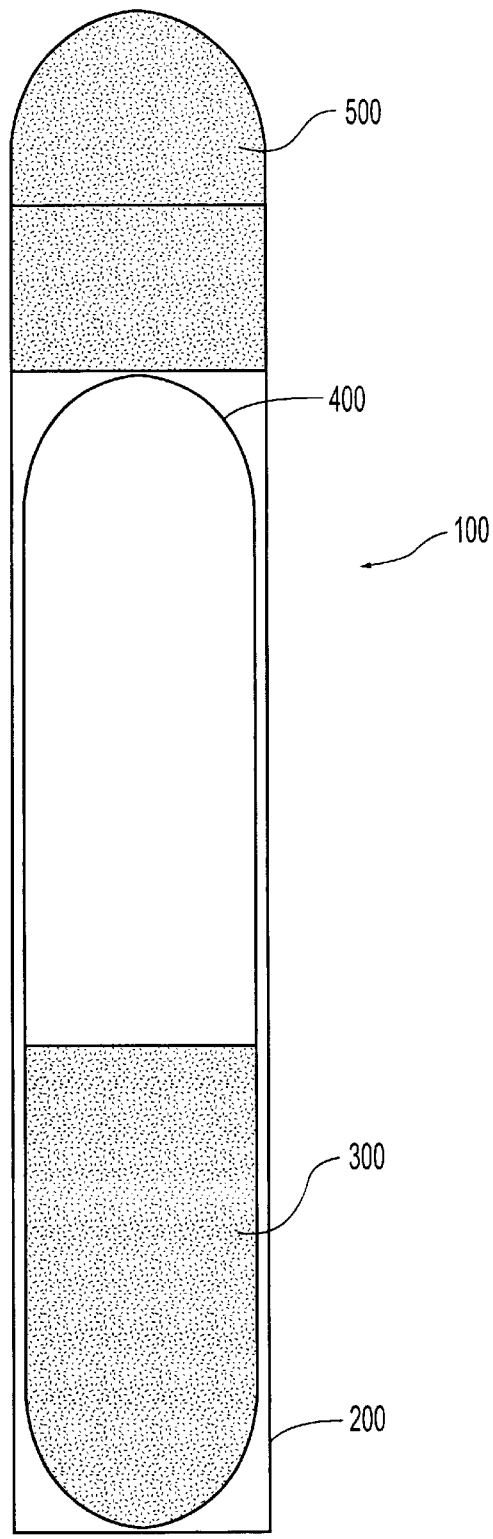
FIG. 1 is a side elevational view of an applicator device according to the prior art.

The present invention provides adhesive applicators with improved applicator tips, suitable for use in a variety of applicator devices including applicator devices of the type shown in FIG. 1, which provide significant improvement in the application and use of adhesive material. Such applicator tips can be used, for example, in combination with the adhesive compositions and packaging and dispensing systems set forth in U.S. Pat. No. 5,928,611, the entire disclosure of which is incorporated herein by reference. Of course, other adhesive compositions, compatible with the applicators of the present invention, can also be used.

To overcome the above disadvantages of the prior art, one approach has been to provide applicator tips that are attachable to an applicator device, where the applicator tip has an open end open toward a container body of the applicator and at least one orifice located at an opposite end of the applicator tip. The open end of the applicator tip overlaps or covers at least a portion of a porous material of the applicator tip, through which the adhesive material is expressed, so that the adhesive is expressed through the porous material, flows through the applicator tip, and exits through the at least one orifice.

Figure 2A:
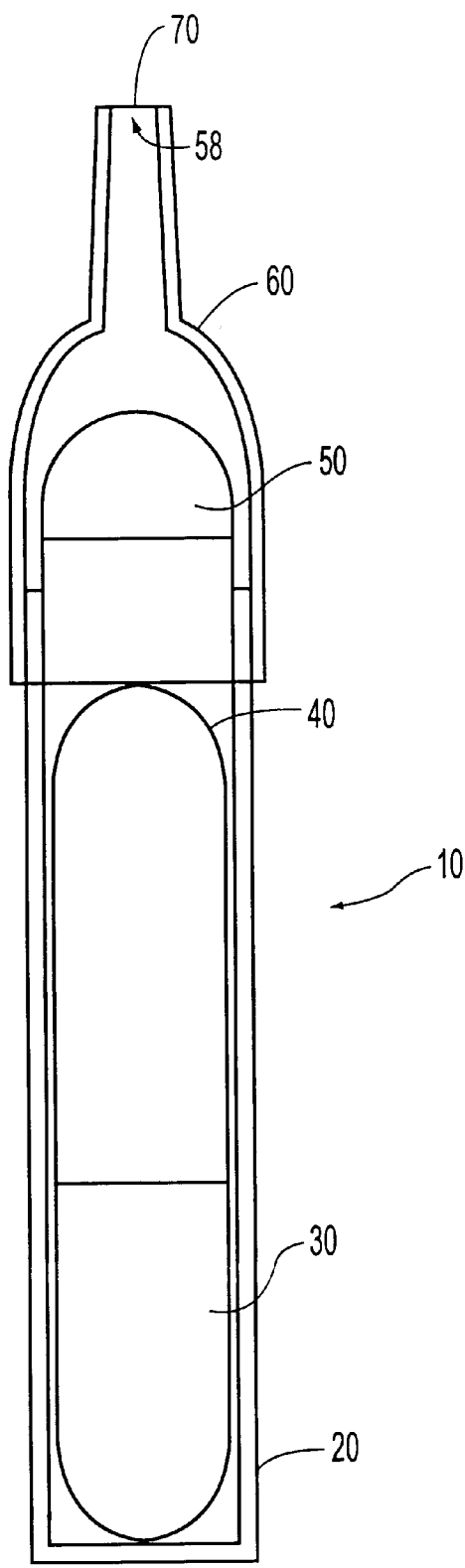
Figure 2B:
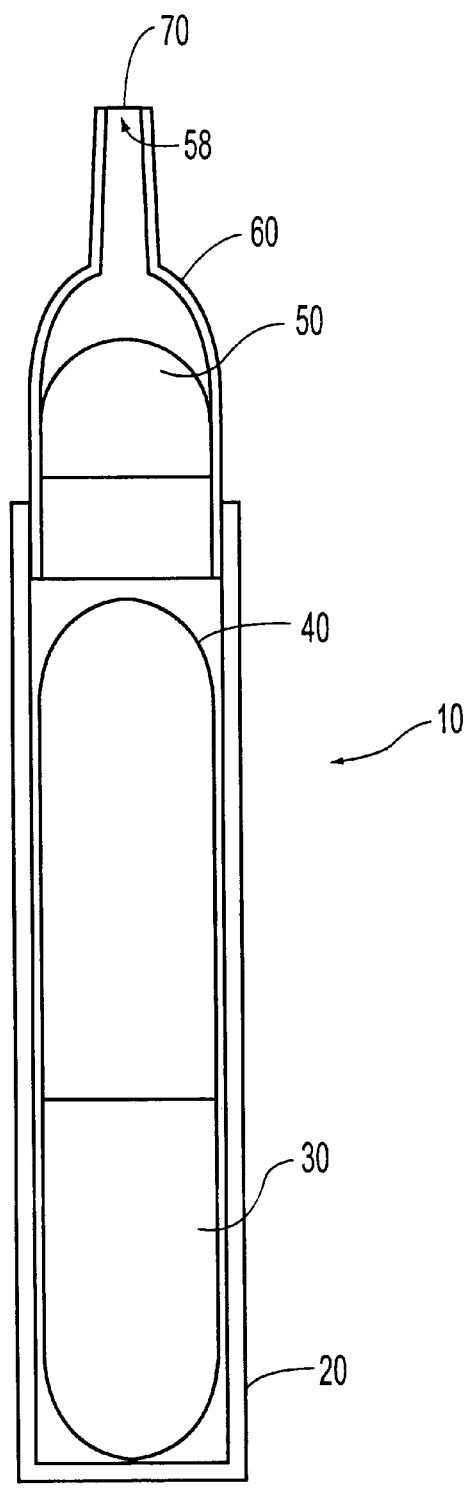

This approach is described, for example, in co-owned U.S. patent application Ser. No. 09/479,060 filed Jan. 7, 2000, the entire disclosure of which is incorporated herein by reference. For example, FIGS. 2a–2d show applicator tips described in the co-pending application. As shown in FIGS. 2a–2d, the applicator device 10 comprises an applicator container or body 20 holding polymerizable and/or cross-linkable adhesive material 30, such as enclosed in a frangible vial 40. One end of the applicator device 10 is sealed, and the other end of the applicator device 10 is fitted with a suitable shaped body of porous material 50, which can contain a polymerization and/or cross-linking initiator for the polymerizable and/or cross-linkable material 30. An applicator tip 60 is attached to the shaped body end of the applicator body. The applicator tip can be attached on the outside of the applicator body, as shown in FIG. 2a, or can be attached on the inside of the applicator body, as shown in FIGS. 2b–2d. The applicator tip 60 has an orifice or opening 70, for dispensing adhesive material from the applicator.

Thus, for example, the porous material 50 can be incorporated into the applicator 10 in various ways. Preferably, when the porous material is included, it is located and/or attached radially inwardly of a portion of the applicator tip 60. Thus, for example, as shown in FIG. 2c, the porous material 50 can be attached directly to an inside surface of the applicator tip 60, which can in turn be attached to an inside surface of the applicator container or body 20, or to an upper rim of the applicator container or body 20.

Alternatively, in embodiments such as shown in FIG. 2d, the porous material 50 can be attached to a holding member 59, which is itself attached to an inner surface of the applicator directly or to an inside surface of the applicator tip 60, which itself is attached to the applicator container or body 20. In these embodiments, the holding member 59 may be formed from any suitable material, and is preferably formed from a material that is less porous and/or less pervious to the adhesive material than is the porous material, and preferably substantially impervious to the adhesive material. The material may be the same or different from the above-described tip materials. Such embodiments may be preferred, for example, where it is desired to provide a narrower passageway for the adhesive material through the porous material or to accommodate optional use of the porous material.

In the applicator tips of FIGS. 2a–2d, the applicator tip has a restrictive flow portion 58 that is located at the orifice 70. As used herein, "restrictive flow portion" means a portion of the applicator tip, or a fluid flow channel from one end of the applicator tip to the orifice end of the applicator tip, that has the narrowest cross-section. This portion of the applicator tip acts to most strongly restrict the flow of adhesive material through the applicator tip. Thus, in the applicator tips shown in FIGS. 2a–2d, the largest flow rate is through the narrowest portion of the applicator tip, which corresponds to the orifice 70.

Although the approach described above provides improved control over placement of the adhesive material to be applied, it continues to pose drawbacks. For example, the large cross-sectional effective surface area difference between the porous material and the orifice/restrictive flow portion of the applicator tip, means that the flow rate through the orifice is much greater than the flow rate through the porous material. As the cross-sectional area of the applicator tip narrows from the porous material to the applicator tip, the flow rate of the adhesive must correspondingly increase. Thus, a moderate pressure applied to the adhesive material to express it through the porous material, results in a large ultimate flow rate through the orifice of the applicator tip. This creates a problem of adhesive exiting too quickly through the orifice, to the point that it may "squirt" out of the applicator tip, rather than smoothly flowing from the applicator tip.

The present invention overcomes this problem by providing a modification to the applicator tip design. That is, the present invention overcomes the increased flow rate problem by providing a flow reducing portion in the applicator tip downstream of the restrictive flow portion of the applicator tip, i.e., at or just prior to the exiting orifice. This is achieved by providing in the applicator tip a portion of the tip that has an increased cross-sectional area as compared to the restrictive flow portion, so that a decreased flow rate is achieved prior to the adhesive material exiting the applicator tip.

According to the present invention, various applicator tips are provided that can be used to more precisely and economically apply adhesive material at the desired application site. Applicator tips of the present invention can be used on any of a wide variety of applicator devices, and are particularly suitable for use on applicator devices disclosed in the above-referenced U.S. Pat. No. 5,928,611. Other known applicator bodies, such as squeeze tubes and syringes, are also amenable to use in some embodiments of the present invention.

The applicator can in all embodiments, but need not in all embodiments, include a shaped body of porous material. The porous shaped body can be, or can be replaced by, a filter element. The filter element can filter out any glass shards or other solids that may be present in the adhesive composition. The filter or porous shaped body may also contain polymerization and/or cross-linking initiators and/or rate modifiers, e.g., accelerators or inhibitors, for the adhesive material, if desired. Suitable porous shaped bodies are disclosed, for example, in U.S. Pat. No. 5,928,611 and in copending application Ser. No. 09/479,059 filed Jan. 7, 2000, the entire disclosures of which are incorporated herein by reference.

In general, applicator tips according to the present invention include a first portion, which is substantially form-fit to a part of the applicator, such as the applicator body, and a second portion, which is substantially not form-fit to the applicator, that forms an extension portion generally away from the applicator body. The first form-fit portion (or proximal end of the applicator tip) facilitates attachment of the applicator tip to the applicator, whereas the second extension portion (or distal end of the applicator tip) provides structure for applying the adhesive material to the desired surface. Preferably, although not required in all embodiments, the first end (or end that attaches to the applicator body) has a larger cross-sectional area than the second end (or orifice from which the adhesive exits the applicator tip).

As used herein, the terms "attach" or "attached" as referring to the applicator tip means operably connecting the applicator tip to the applicator body, or parts thereof, directly or through other components. Thus, for example, the applicator tip can be attached to the applicator body in any suitable way, including but not limited to mechanical arrangements such as luer locks, threads, one or more concentric ribs, or locking rings, pressure and/or friction fitting, adhesive or chemical arrangements such as adhesive or chemical bonding, heat-shrink attachment, ultrasonic welding, and the like.

The applicator tip is generally of a rigid or semi-rigid material, to permit controlled delivery of the monomeric adhesive material to the desired application site. Suitable materials for forming the applicator tip include, but are not limited to, natural materials such as cellulose, cardboard, metal, ceramic, glass, plastics such as butyrate or high density polyethylene, polypropylene, polyester, or the like. Preferably, the applicator tip is made of a non-porous material and has a decreased affinity for the monomeric adhesive. That is, the applicator tip preferably does not readily absorb or adsorb large amounts of the monomeric adhesive material being expressed through the applicator tip, which would otherwise tend to leave residual material in the applicator tip. Less porosity of the applicator tip is preferred because it has been found that when the porous member is exposed to the environment, adhesive material being expressed through the porous member tends to harden and clog the porous member in the exposed areas. However, by using a less-porous material attached to the porous member, and having less of the porous member exposed to the environment, the problem of hardening and clogging in the porous member can be decreased or avoided.

Figure 3A:
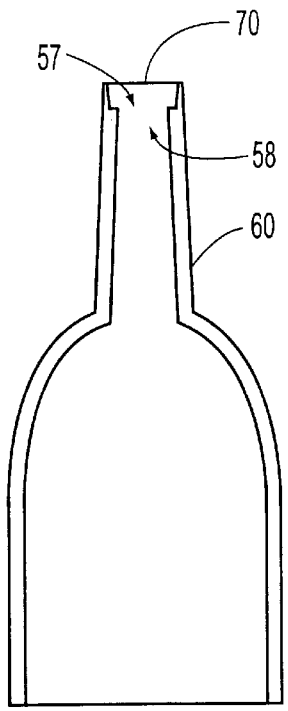
FIGS. 3a–3d are side elevational views of applicator tip designs according to the present invention.
Figure 3B:
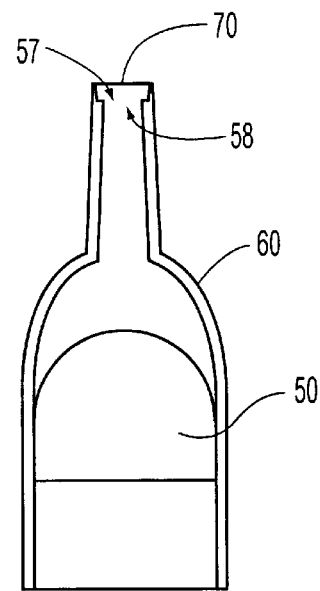
Figure 3C:
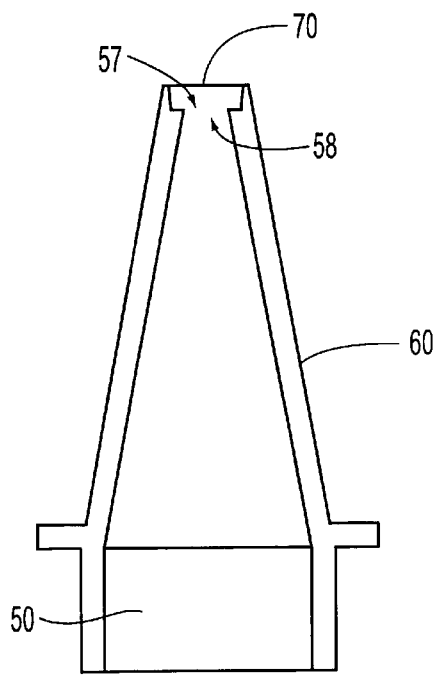
Figure 3D:
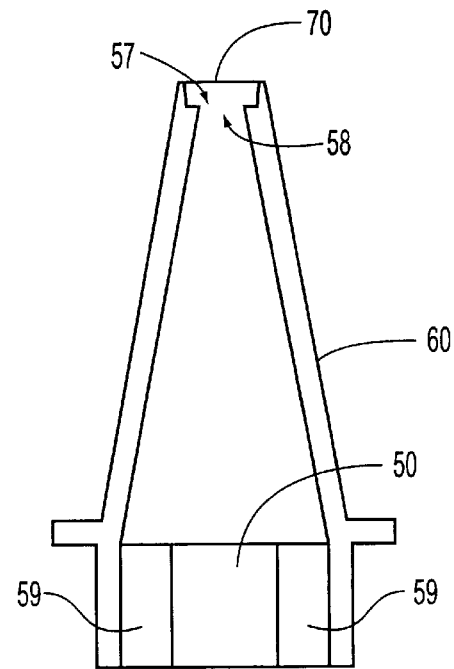

Exemplary embodiments of applicator tips according to the present invention are shown in FIGS. 3a–3d, although according to embodiments of the present invention, the applicator can generally assume different shapes and designs, as desired. The applicator tips of FIGS. 3a–3d generally correspond to the applicator tips 60 shown in FIGS. 2a–2d, respectively, although modified to include the improvement of the present invention. In FIGS. 3a–3d, the applicator tip 60 includes a modification at the orifice portion 70 that causes a decrease in the flow rate of the adhesive as it exits the applicator tip. In particular, the applicator tip 60 is modified at the orifice end 70 to include a flow reducing portion 57 to thereby provide a greater cross-sectional area for the adhesive to flow through prior to exiting the applicator tip, as compared to an upstream section of the applicator tip. In the embodiments of the present invention, the applicator tip includes both a restrictive flow portion and a flow reducing portion, where the flow reducing portion is located downstream of the restrictive flow portion (i.e., between the restrictive flow portion and the orifice). Although the applicator tip is shown in FIGS. 3b–3d as including the porous solid support 50, such porous solid support 50 is not required in all embodiments and is shown only for comparison to FIGS. 2a–2d.

Figure 4:
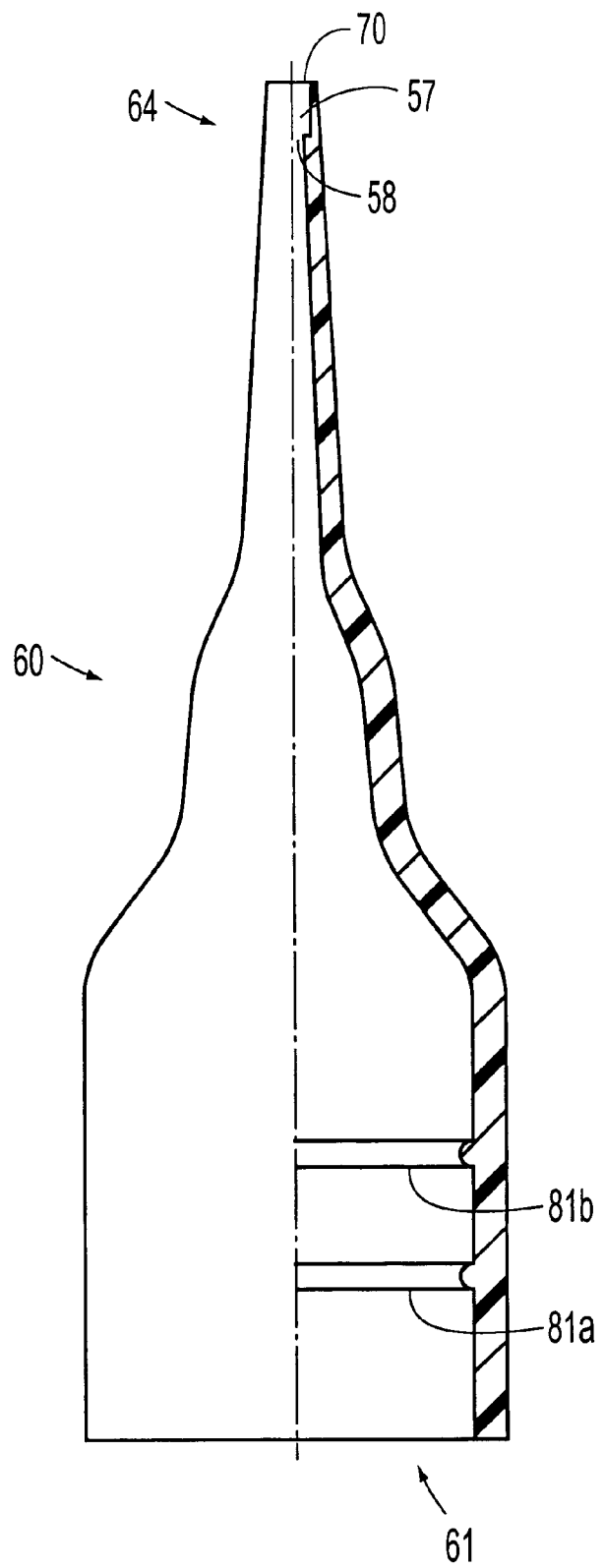
FIG. 4 is a cross-sectional view of an applicator tip according to the present invention.

A particular embodiment of an applicator tip according to the present invention is shown in FIG. 4. In FIG. 4, the applicator tip 60 includes a first end 61 and a second end 64. The first end 61 is shaped and sized appropriately for attachment to a suitable adhesive applicator (not shown). The first end 61 is also shown as including first and second ribs 81a,81b to assist in attachment of the applicator tip to an applicator body, although it will be understood that one or more ribs are not required, and attachment can be accomplished by various other means. The second end 64, which includes the orifice 70, is shaped and sized for desired application parameters of the adhesive material. As shown in FIG. 4, the cross-sectional area of the applicator tip generally decreases from the first end 61 to the second end 64. However, at the second end 64, the cross-sectional within the applicator tip is increased, for example, by thinning the wall material at the second end 64. Thus, the second end 64 includes both the restrictive flow portion 58 followed by a flow reducing portion 57. This thinning of the wall material to form the flow reducing portion 57 provides a greater cross-sectional area, and thus a lower flow rate, at the orifice 70 than in a preceding portion of the applicator tip.

Figure 5A:
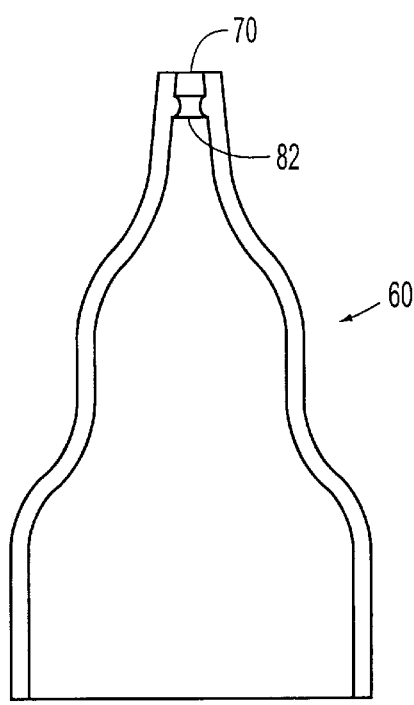
FIGS. 5a–5d are cross-sectional views of applicator tips according to embodiments of the present invention.
Figure 5B:
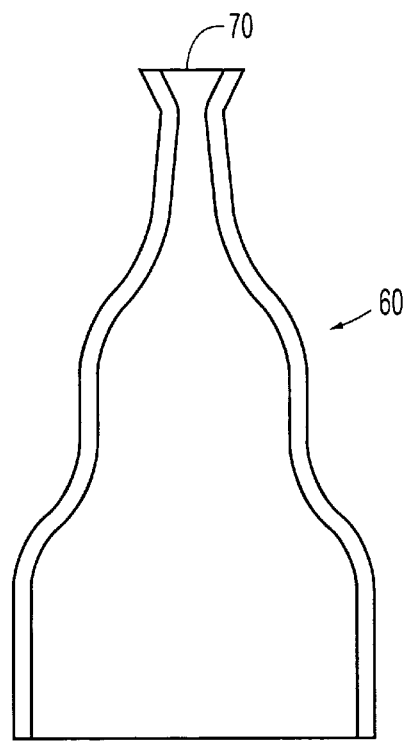
Figure 5C:
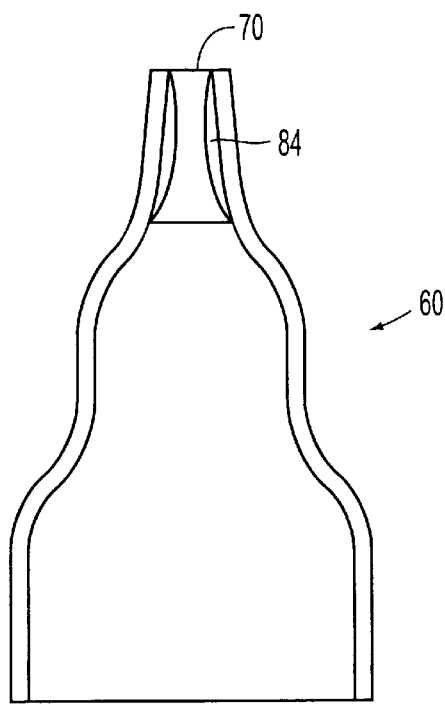
Figure 5D:
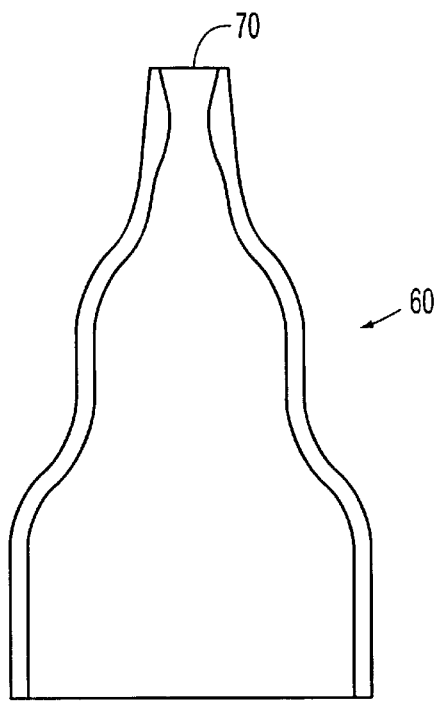

Of course, the greater cross-sectional area and reduced flow rate can be provided other than by thinning out the wall material of the applicator tip. For example, FIGS. 5a–5c show alternative embodiments where the greater cross-sectional area is provided in alternative ways. In FIG. 5a, a greater cross-sectional area is provided by including a rib 82 in the design just prior to the orifice 70. In FIG. 5b, a greater cross-sectional area is provided by keeping the wall thickness of the applicator tip substantially constant, but by increasing the diameter of the applicator tip at the orifice end. In FIG. 5c, a greater cross-sectional area is provided by inserting a flow controller block 84 into the orifice end of the applicator tip. This flow controller block can be made of any suitable material. A modification of the embodiment of FIG. 5c (and FIG. 4) is shown in FIG. 5d, where the cross-sectional area is provided by making the applicator tip wall thicker at the orifice end, such that the walls protrude further into the flow channel to alter the cross-sectional area of the flow channel. Any of these alternatives, as well as others, can be utilized according to the present invention to provide an applicator tip design where a flow reducing portion is located downstream in a fluid-flow direction of the restrictive flow portion.

Of course, numerous other methods can be used to provide a greater cross-sectional area at an orifice end of the applicator tip. Such other methods are encompassed by the present invention, which is not limited to the above-described embodiments.

According to the present invention, the cross-sectional area of the flow channel provided in the applicator tip preferably decreases from the proximal end to the restrictive flow portion of the applicator tip. Thus, for example, the cross-sectional area can decrease progressively (i.e., non-constantly) as shown in FIG. 4, or it can decrease constantly, such as shown in FIGS. 3a–3d. However, other geometries can be readily adapted for use in applicators and are encompassed by the present invention. Likewise, it is preferred in embodiments that the flow reducing portion provide a cross-sectional area for fluids flow that is smaller than a cross-section area of the proximal end of the applicator tip, although the invention is in no way limited to such dimensions.

Figure 6A:
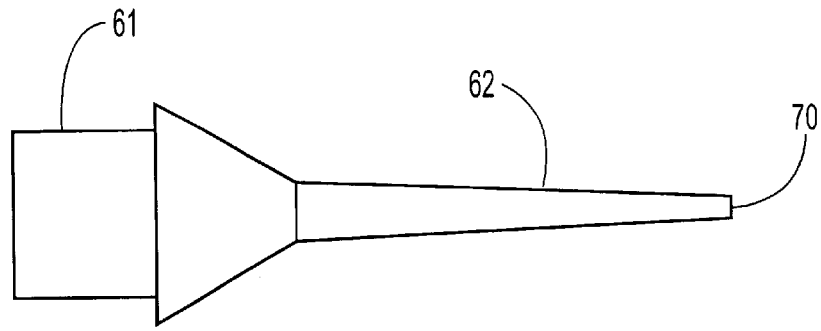
FIGS. 6a–6c are elevational views of applicator tip designs according to the present invention.
Figure 6B:
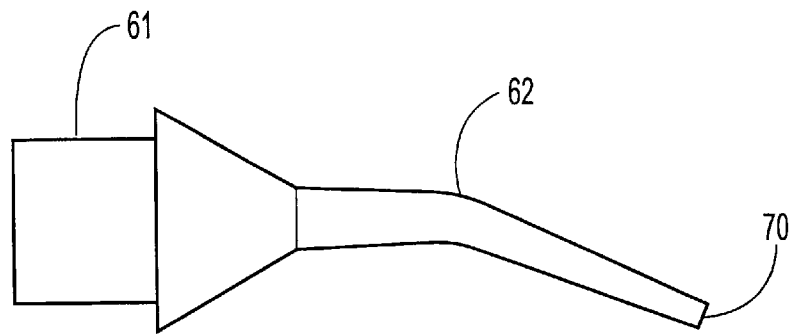
Figure 6C:
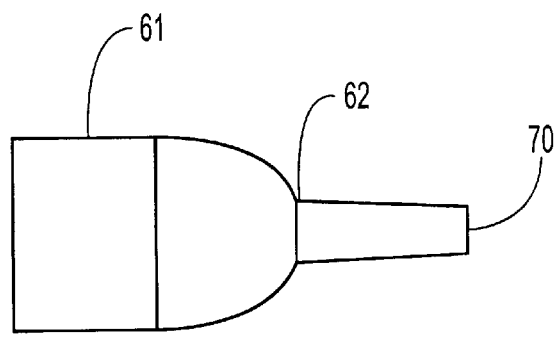

As shown in FIGS. 6a–6c, the applicator tip 60 includes a connection portion 61, located at the proximal end of the applicator tip where the applicator tip attaches to the applicator body, and an extension or application portion 62, located toward the distal end of the applicator tip. As used herein, the proximal end refers to the end of the applicator tip that is attached to, inserted into, or closest to the applicator body, and the distal end refers to the opposite end of the applicator tip. An orifice 70, which may be of any desired shape and size, is generally located at the end of the application or extension portion 62. For example, FIG. 6a shows the applicator tip as having a fine orifice 70 at the distal end of the applicator tip, suitable for applying a fine line of adhesive, or for applying adhesive with high accuracy of placement. The applicator tip of FIG. 6b is similar to the applicator tip of FIG. 6a, but shows that the applicator tip can be bent at any desired angle, to provide ease of use in applying the monomeric adhesive material to the desired surface and/or for applying the monomeric adhesive material in confined spaces. Likewise, FIG. 6c shows that the orifice can be of a larger size, for example for cases where a thicker line or area of adhesive is to be applied.

According to the present invention, the applicator tip can have any desired length, so long as the applicator tip is still effective in dispensing the monomeric adhesive material. Thus, for example, the applicator tip should not be so long so as to be ineffective in delivering the monomeric adhesive material through the tip. Likewise, the orifice can be of any desired size, and can be adjusted for various desired applications. Preferably, the orifice should be sized such as to provide enough resistance to flow of the adhesive material therethrough that the adhesive material does not exit on its own such as when the applicator is inverted. Of course, as will be apparent, the orifice dimensions will accordingly depend on the viscosity of the adhesive material.

Figure 7:
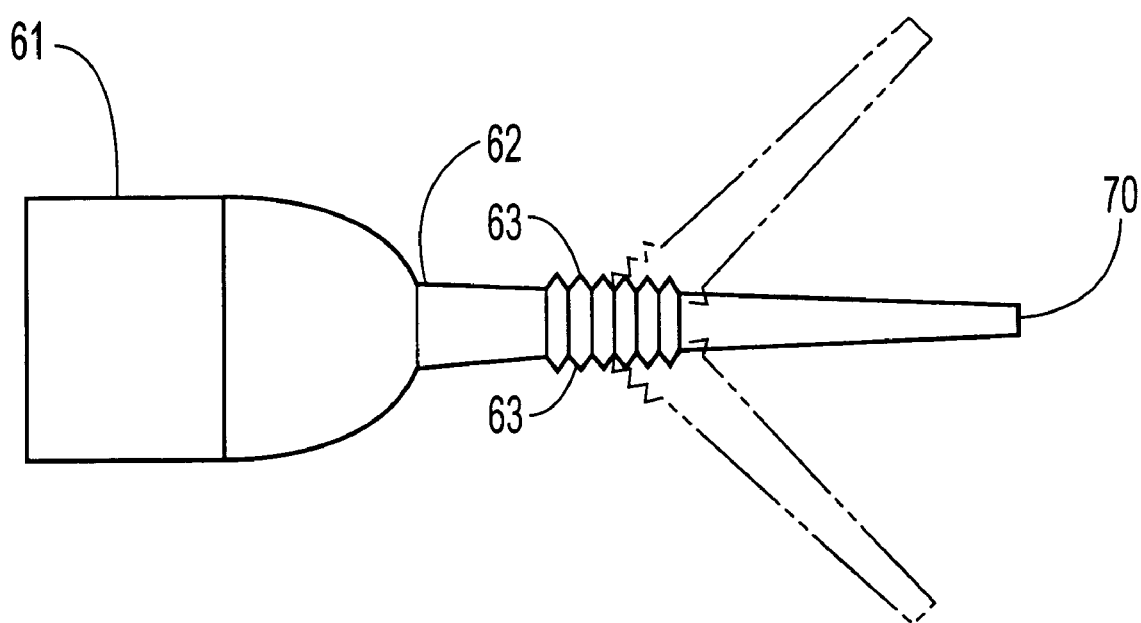
FIG. 7 is an elevational view of an applicator tip according to the present invention including an accordian section.
Figure 8A:
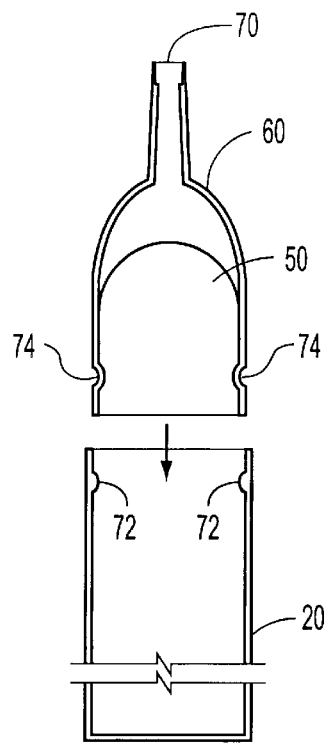
FIGS. 8a–8d are elevational views showing attachment of an applicator tip to an applicator body.
Figure 8B:
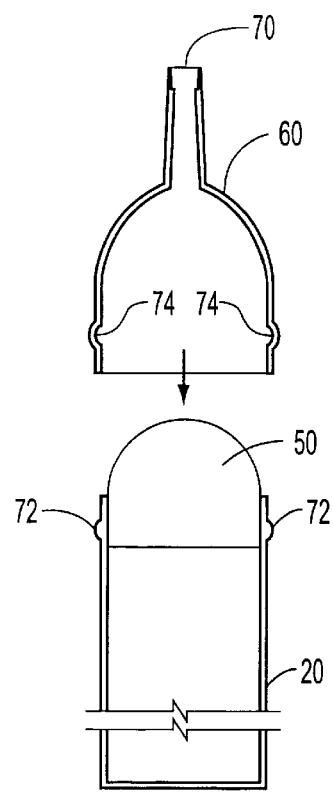
Figure 8C:
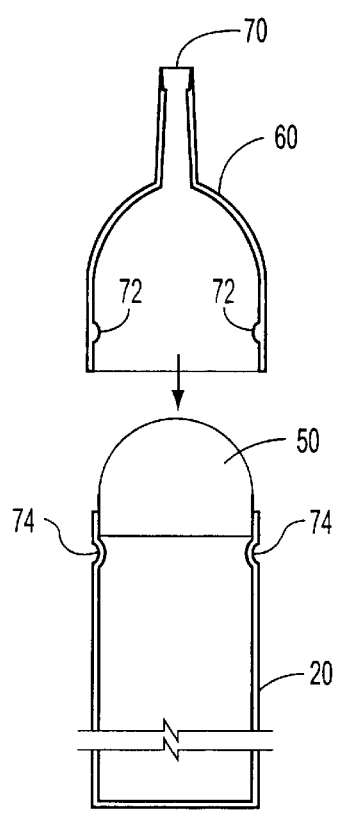
Figure 8D:
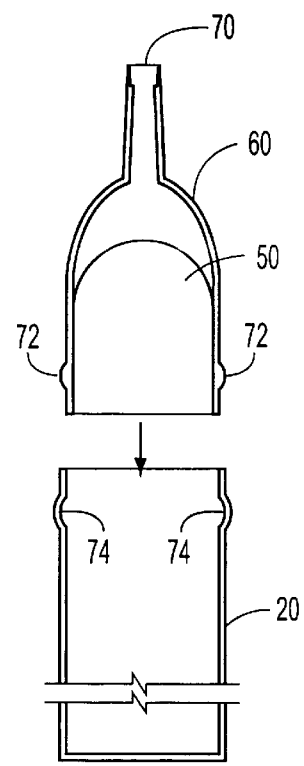

In embodiments of the present invention, the applicator tip can be provided with one or more accordian-type sections, which permit expansion or contraction of the applicator tip length, and/or adjustment of the applicator tip shape by the user. Such an embodiment is shown, for example, in FIG. 7. FIG. 7 shows the applicator tip as including a connection portion 61, an extension or application portion 62, and an orifice 70. FIG. 7 also shows the presence of an accordion portion 63. Adjustment of the accordion portion allows the applicator tip to be extended or contracted, or to be rotated to various angles with respect to the applicator body.

Thus, use of such an accordian section in the applicator tip, or other suitable expansion/bending mechanism, provides significant benefits to the applicator system as a whole. In particular, the accordian design permits the user to adjust the length and shape of the applicator tip to any desired amount, thereby allowing the user to tailor the applicator device to the circumstances of any given use. Furthermore, packaging of the applicator device is simplified, because the shorter, compressed, straight applicator tip is small and more compact than a longer, expanded, bent applicator tip.

According to the present invention, the applicator tip can be permanently or replaceably attached to the applicator body in various ways. For example, the applicator tip can be attached to the applicator body either on the outside of the applicator body, or on the inside of the applicator body. In both instances, the applicator tip can be, for example, adherently bonded to the applicator body, can be attached to the applicator body by heat-shrinking the applicator tip onto the applicator body or heat-shrinking the applicator body onto the applicator tip, can be attached onto or into the applicator body by suitable mechanical means, including luer locks, threads or locking rings (not shown) or can be held to the applicator body by pressure and/or friction. Adherent or heat-shrink attachment may be preferred in embodiments where the applicator tip is not to be interchangeable, or where the applicator tip is attached during the manufacturing process. However, screw, locking or friction/pressure attachment may be preferred in embodiments where interchangeability is desired, such as where different sizes or types of applicator tips are available for a given applicator body. Such interchangeable tips can be used, for example, to provide possible selection of different application profiles of the adhesive material.

One particularly suitable means for attaching the applicator tip to the applicator body is to use snap edges or locking rings on one of the applicator body or the applicator tip, with mating members on the other of the applicator body or the applicator tip. For example, suitable configurations for attaching an applicator tip to an applicator body are shown in FIGS. 8a–8d. In each of FIGS. 8a to 8d, the applicator is shown as having an applicator body 20, a porous shaped body 50, and an applicator tip 60 having an orifice 70. Each of the applicators also has a male mating ring or tabs 72 or a female mating ring or recesses 74, and the applicator tip has the other of the male mating ring or tabs 72 or a female mating ring or recesses 74. Thus, for example, the applicator tip 60 snaps over the applicator body 20 in the embodiments of FIGS. 8b and 8c, while the applicator tip 60 snaps into the applicator body 20 in the embodiments of FIGS. 8a and 8d. Of course, these embodiments are not limited to the use of mating rings or tabs, as shown in FIGS. 8a–8d, but instead apply to various structures for attaching the applicator tip to the applicator body.

Although the above embodiments have been described as being directed to an applicator wherein the applicator body is a sealed vessel that includes a frangible ampoule containing the adhesive material, the invention is not limited to such embodiments. Rather, the applicator tips of the present invention can be used on a wide variety of adhesive dispensing applicators.

For example, the applicator tips of the present invention can be used in combination with an applicator where the applicator body includes a relatively larger supply of adhesive material. Such an applicator is particularly useful, for example, where the adhesive material is not a highly polymerizable material, and where the same supply of adhesive material can be used for multiple adhesive applications from the same applicator.

Applicator tips of the present invention can be used in combination with an applicator where the applicator body includes a container of adhesive material that is broken by a suitable structure in the applicator prior to use. This embodiment, for example, is useful where the adhesive material is contained in a rupturable container, which can be contained in a closed applicator body, or which can be inserted into an open end of an applicator body and is subsequently ruptured for use. For example, the container could be ruptured by a suitable projection attached to the porous shaped body and/or the applicator tip but projecting into the applicator body. Such embodiments are shown, for example, in the above-cited co-pending U.S. patent application Ser. No. 09/479,060, the entire disclosure of which is incorporated herein by reference.

Figure 9:
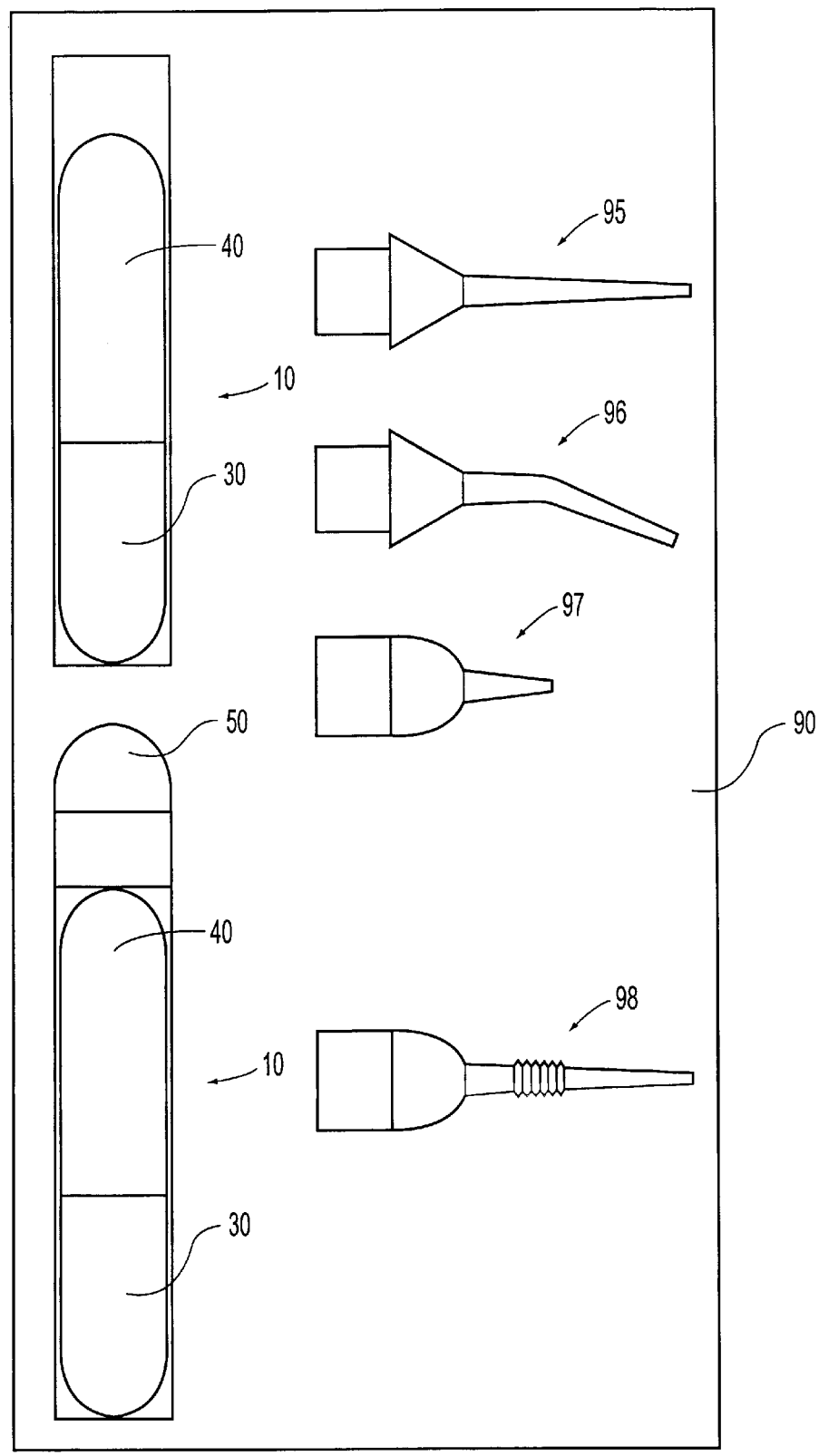
FIG. 9 is a side elevational view of a kit according to the present invention.

According to embodiments of the present invention, use of non-permanent means of attaching the applicator tip to the applicator body are preferred for purposes of interchangeability. For example, interchangeable tips may give the user of the applicator the ability to select a desired applicator tip size and/or design for particular applications. Thus, the present invention provides for kits for dispensing adhesive material, where the kit can include one or more applicators or adhesive containers, and two or more applicator tips that are attachable to the adhesive containers. Preferably, as shown in FIG. 9, such kits will include one or more adhesive containers 10 and multiple applicator tips 95–98 of different sizes and/or designs in a saleable package 90, such as a blister pack, cardboard box, or the like, and will include more applicator tips than adhesive containers. Such kits can include any combination of the applicators and applicator tips.

In embodiments, the kit preferably includes a greater number of applicator tips than adhesive containers. In other embodiments, the kit can include the same number of applicator tips as adhesive containers, but the applicator tips can be of different sizes and/or different shapes. This allows the user to select an appropriate applicator tip based on the desired use of the adhesive material.

The contents of the kit can be packaged in any of a variety of ways, depending on the desired uses, marketing considerations, and the like. For example, the adhesive container and applicator tip can be packaged, such as in appropriate blister packs, individually, or in together in a combination package. Likewise, multiple individually packaged adhesive containers and/or applicator tips can be packaged together, such as in a bulk carton or in blister packs attached together at parting lines such as perforated parting lines.

According to the present invention, the applicator can include any suitable adhesive material. The adhesive material can include monomeric (including pre-polymeric) materials, polymeric materials, or mixtures thereof. The monomer (including prepolymeric) adhesive composition may include one or more polymerizable monomers. Preferred adhesive compositions for use in applicators of the present invention are useful as tissue adhesives, sealants for preventing bleeding or for covering open wounds, and in other biomedical applications. They find uses in, for example, apposing surgically incised or traumatically lacerated tissues; retarding blood flow from wounds; dressing burns; dressing skin or other superficial or surface wounds such as compromised skin or other tissue (such as abrasions, chaffed or raw skin, minor cuts and scrapes, sores and/or ulcers such as stomatitis); protecting intact skin; and aiding repair and regrowth of living tissue. Adhesive compositions of the present invention are also useful in industrial and home applications, for example in bonding rubbers, plastics, wood, composites, fabrics, and other natural and synthetic materials.

Preferred monomers that may be used in this invention are readily polymerizable, e.g. anionically polymerizable or free radical polymerizable, or polymerizable by zwitterions or ion pairs to form polymers. Such monomers include those that form polymers, that may, but do not need to, biodegrade. Such monomers are disclosed in, for example, U.S. Pat. No. 5,328,687 to Leung, et al., which is hereby incorporated in its entirety by reference herein.

Particularly preferred adhesive materials are 1,1-disubstituted ethylene monomers including, but not limited to, monomers of the formula:

$$HRC=CXY \quad (I)$$

wherein X and Y are each strong electron withdrawing groups, and R is H, —CH=CH$_2$ or, provided that X and Y are both cyano groups, a $C_1$–$C_4$ alkyl group. Examples of monomers within the scope of formula (I) include α-cyanoacrylates, such as ethyl, butyl and/or 2-octyl cyanoacrylate, vinylidene cyanides, $C_1$–$C_4$ alkyl homologues of vinylidene cyanides, dialkyl methylene malonates, acylacrylonitriles, vinyl sulfinates and vinyl sulfonates of the formula CH$_2$=CX'Y' wherein X' is —SO$_2$R' or —SO$_3$R' and Y' is —CN, —COOR',—COCH$_3$, —SO$_2$R' or —SO$_3$R', and R' is H or hydrocarbyl.

Furthermore, the adhesive composition contained in the applicator can further include various additives as are known in the art, including but not limited to flavorants, preservatives, plasticizing agents, stabilizing agents, formaldehyde concentration reducing agents, pH modifiers, thickening agents, cross-linking agents, fibrous reinforcement agents, colorants, and the like.

Suitable compositions, methods of making such compositions, and methods for incorporating such compositions into a dispenser device are described, for example, in U.S. Pat. No. 5,928,611 to Leung; U.S. Pat. Nos. 5,328,687, 5,514,371, 5,514,372, 5,575,997, 5,582,834 and 5,624,669, all to Leung et al; U.S. Pat. No. 5,259,835 to Clark et al.; U.S. Pat. No. 3,527,841 to Wicker et al.; U.S. Pat. No. 3,722,599 to Robertson et al.; U.S. Pat. No. 3,995,641 to Kronenthal et al.; and U.S. Pat. No. 3,940,362 to Overhults; and U.S. patent application Ser. Nos. 08/266,647, 08/714,288, 09/099,457, 09/430,177, and (100497.02 filed Oct. 29, 1999), the entire disclosures of which are incorporated herein by reference.

According to the present invention, the porous shaped body, whether integral with or used in combination with the applicator tip, may, but need not, include a polymerization and/or cross-linking initiator and/or rate modifier, such as an accelerator or inhibitor, for a polymerizable monomer adhesive material contained in the applicator. Suitable polymerization and/or cross-linking initiators and rate modifiers, and methods for applying them to the applicator tip, are described in, for example, U.S. Pat. No. 5,928,611 and U.S. patent application Ser. No. 09/430,177, filed Oct. 29, 1999, Ser. Nos. 09/430,176, 09/430,289, 09/430,290, and 09/430,180 filed Oct. 29, 1999; Ser. No. 09/343,914 filed Jun. 30, 1999; Ser. No. 09/385,030 filed Aug. 30, 1999; and Ser. No. 09/176,889 filed Oct. 22, 1998, the entire disclosures of which are incorporated herein by reference. Preferred initiators for some medical uses include benzalkonium chloride, and for some industrial uses include dimethyl toluidine.

The polymerization and/or cross-linking initiator and/or rate modifier may be applied to the porous shaped body by any suitable means, including, but not limited to, spraying, dipping, injecting, or brushing the porous shaped body with a liquid medium containing the polymerization and/or cross-linking material. It is preferably applied by dipping or injecting. For example, it may be applied by pumping of the liquid medium, for example, through a syringe, onto the distal end of the porous shaped body.

The polymerization and/or cross-linking initiator and/or rate modifier may be applied to the porous shaped body by using a vacuum or pressure process. In each process, a solution or suspension of the polymerization and/or cross-linking initiator and/or rate modifier is introduced into a vacuum or pressure chamber. One or more porous shaped bodies, either individually or preferably in batches, are placed into the solution or suspension in the pressure vessel in a manner such that they preferably do not float to the top of the solution or suspension. For example, they can be placed in the solution or suspension in a wire basket or other suitable container, which would hold them under the solution or suspension, or a wire mesh or other suitable retainer could be placed over them to dunk or sink them into the solution or suspension. Once they are in the solution or suspension, the vessel can be sealed and an appropriate vacuum or pressure applied.

Application of the vacuum or pressure results in air that is trapped in the porous shaped bodies being degassed, or forced out of the porous shaped bodies, and being replaced by the solution or suspension. This replacement of air by the solution or suspension thereby loads the material onto or into the porous shaped bodies. The end of the degassing phase can be observed by the absence of newly formed air bubbles. After a desired treatment time, the vacuum or pressure in the vessel can be released, and the treated porous shaped bodies can be removed.

In exemplary embodiments, preparing an applicator for dispensing polymerizable monomeric compositions includes applying a material to a suitable porous shaped body, such as a porous polyethylene, foam or fibrous tip, which is attached to an applicator body, such as a butyrate applicator tube or other suitable holder.

In addition to the polymerization and/or cross-linking initiator and/or rate modifier, the porous shaped body and/or applicator tip can also include various other materials that may or may not act as a polymerization initiator and/or rate modifier. For example, they can include a flavorant, such that it imparts a flavor to the adhesive material when the adhesive material is applied to a surface. Incorporation of a flavorant is particularly preferred, for example, when the cyanoacrylate adhesive material is to be applied to oral surfaces, such as to treat ulcers such as stomatitis or cold sores. Similarly, they can include a bioactive material, which may or may not also be a polymerization and/or cross-linking initiator and/or rate modifier. Examples of suitable bioactive materials include, but are not limited to, medicaments such as antibiotics, antimicrobials, antiseptics, bacteriocins, bacteriostats, disinfectants, steroids, anesthetics, antifungal agents, anti-inflammatory agents, antibacterial agents, antiviral agents, antitumor agents, growth promoting substances, antioxidants, or mixtures thereof.

The porous shaped body may be composed of any of a variety of materials including polymerized materials such as plastics, foams, rubber, thermoset resins, films, fibers, or membranes. Where foams are used, the foam can be either an open-celled form, a closed-cell foam, or a mixture thereof. Any suitable foam material can be used and suitable foams include, for example, thermoplastic polyurethane foam, preferably a soft, absorbent thermoplastic polyurethane foam.

In embodiments, the porous shaped body may be made from polyurethane, polyesters, polyolefins such as polyethylene, or polyamides. In embodiments, it may be made from polyethylene, such as that sold by Porex Technologies Corp. (Fairburn, Ga.) under the trademark LabPor®. In embodiments, the porous shaped body can also be made from fibers, either natural or synthetic, such as cotton, rayons, nylons, and mixtures thereof. Additionally, the porous shaped body may be composed of materials such as metal, glass, paper, ceramics, and the like. It may be absorbent or adsorbent in nature to enhance and facilitate loading of a material on or in the applicator tip. For example, the porous shaped body may be composed of a material having random pores, capillaries, a honeycomb material, a material having a woven pattern, etc. The degree of porosity will depend on the materials being used, and can be determined by one of ordinary skill in the art without undue experimentation. Porosity is the open volume within the pores of a porous shaped body divided by the total volume of the porous shaped body.

In embodiments, the porous shaped body may have an average pore size of about 1 $\mu$m to about 500 $\mu$m. Generally, according to the present invention, an average pore size of about 1–100 $\mu$m such as 10–30 is used with a polymerizable material having a viscosity of about 1–30 cP, preferably about 2–18 cP, and more preferably 5–7 cP at 25° C. An average pore size of from about 1 $\mu$m to about 100 $\mu$m is preferably used with a polymerizable material having a viscosity of about 10–30 cP. When the polymerizable and/or cross-linkable material has a viscosity higher than 7 cP, the average pore size is generally increased. For example, an average pore size of about 40–300 $\mu$m such as 60–125 $\mu$m is preferably used with a polymerizable material having a viscosity of about 30–500 cP, preferably about 35–350 cP, and more preferably about 50–200 or 60–140 cP at 25° C. In embodiments, the pore volume is less than or equal to 80 percent, preferably between 20–60 percent.

In embodiments of the present invention, the adhesive composition has a viscosity of about 1–5000 centipoise, preferably 1–600 centipoise, more preferably 1–100 or 2–50 centipoise such as 2–18, 2–10 or 5–7 centipoise, or 30–500 such as 50–100 or 100–200 centipoise at 25° C. The viscosity can be selected according to the proposed use— e.g., 1–100 centipoise for certain uses and 100–200 centipoise for other uses. Additionally, the composition may be a gel, e.g., 50,000–500,000 centipoise at 25° C. The viscosity of the adhesive composition can be measured with a Brookfield Viscometer. Additionally, in embodiments where a sterilization treatment is applied, the viscosity of the composition should preferably be maintained or increased by a controlled and acceptable amount after sterilization.

When the applicator tip and/or applicator includes a shaped body of porous material, the composition preferably is not expressed directly through the shaped body in a continuous motion. According to embodiments of the present invention, the adhesive composition is (1) expressed to the end or part way to the end of the porous material, (2) the pressure is released to draw the composition back into the applicator, and (3) the composition is then subsequently expressed through the applicator tip in a continuous motion. This is called a suck-back method of applying the adhesive composition of the present invention. When used with a porous material that bears an initiator, this method lets the adhesive composition polymerize better than if it had been expressed directly through the tip.

Once the applicator assembly is prepared, the assembly (or individual components thereof) can be sterilized according to known practices. Compatibility of the adhesive composition, the applicator, the applicator tip, the porous shaped body, and the packaging, with one or more sterilization procedures is preferred in embodiments of the present invention because many uses of the adhesive compositions, such as many surgical and other medical applications, require sterilized products. In preferred embodiments, there is substantially no initiation of polymerization of monomeric liquid adhesive compositions that affects the utility of the monomer or monomers caused by the sterilization process, even when repeated sterilization steps are applied.

Sterilization of the monomer composition and/or its packaging can be accomplished by techniques known to the skilled artisan, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, gamma irradiation, electron beam irradiation, and microwave irradiation. A preferred method is electron beam irradiation. In embodiments where a composition is to be used for medical applications, the sterilized composition must show low levels of toxicity to living tissue during its useful life.

While the invention has been described with reference to preferred embodiments, the invention is not limited to the specific examples given, and other embodiments and modifications can be made by those skilled in the art without departing from the spirit and scope of the invention.

What is claimed is:

1. An applicator for dispensing adhesive material, comprising:
   a container body,
   an adhesive material located in said container body, wherein said adhesive material is a polymerizable or cross-linkable monomer material, and
   an applicator tip, wherein said adhesive material is located in said container body in a non-contacting relationship with said applicator tip prior to dispensing said adhesive material,
   said applicator tip having a proximal open end open toward said container body for attachment to said container body, a distal end having at least one orifice, a restrictive flow portion located between said proximal end and said distal end, and a flow reducing portion located between said restrictive flow portion and said distal end,
   said applicator tip defining a fluid flow channel from said proximal end to said distal end and through said restrictive flow portion and said flow reducing portion,
   wherein said applicator tip permits said adhesive material to pass through said applicator tip and exit said applicator tip at said at least one orifice,
   and further comprising a shaped body of porous material, wherein said adhesive material is located in said container body in a non-contacting relationship with said porous material prior to dispensing said adhesive material, and wherein said applicator tip permits said adhesive material to pass through said porous material and exit said applicator tip at said at least one orifice.

2. The applicator according to claim 1, wherein a cross-sectional area of said channel at said orifice is greater than a cross-sectional area of said channel at said restrictive flow portion.

3. The applicator according to claim 1, wherein at least a portion of said porous material is located in said open end of said applicator tip.

4. The applicator according to claim 1, wherein said restrictive flow portion is located close to said distal end than to said proximal end.

5. The applicator according to claim 1, wherein a cross-sectional area of said channel at said orifice is greater than a cross-section area of said channel at said proximal end.

6. The applicator according to claim 1, wherein a cross-sectional area of said channel progressively decreases from said proximal end to said restrictive flow portion.

7. The applicator according to claim 1, wherein a cross-sectional area of said channel constantly decreases from said proximal end to said restrictive flow portion.

8. The applicator according to claim 1, wherein said applicator tip is attached to an outside surface of said container body.

9. The applicator according to claim 8, wherein said applicator tip is attached to said container body by at least one of an adhesive material, chemical bonding, and ultrasonic welding.

10. The applicator according to claim 8, wherein said applicator tip is attached to said container body by heat-shrinking a portion of the applicator tip onto said container body.

11. The applicator according to claim 8, wherein said applicator tip is attached to said container body by one of pressure, friction fitting, threads, and luer locks.

12. The applicator according to claim 1, wherein said porous material is attached to an inside surface of said container body.

13. The applicator according to claim 1, wherein said porous material is attached to an inside surface of said applicator tip.

14. The applicator according to claim 1, wherein said porous material is attached to a holding member, and said holding member is attached to said applicator tip.

15. The applicator according to claim 14, wherein said holding member is substantially impervious to said adhesive material.

16. The applicator according to claim 1, wherein said applicator tip is attached to an inside surface of said container body.

17. The applicator according to claim 16, wherein said applicator tip is attached to said container body by at least one of an adhesive material, chemical bonding, and ultrasonic welding.

18. The applicator according to claim 16, wherein said applicator tip is attached to said container body by heat-shrinking a portion of said container body onto a portion of the applicator tip.

19. The applicator according to claim 16, wherein said applicator tip is attached to said container body by at least one of pressure, friction fitting, threads, and luer locks.

20. The applicator according to claim 1, wherein said fluid flow channel has a longitudinal axis that is substantially parallel to a longitudinal axis of said applicator.

21. The applicator according to claim 1, wherein said fluid flow channel has a longitudinal axis that is not substantially parallel to a longitudinal axis of said applicator.

22. The applicator according to claim 1, wherein said applicator tip comprises at least one accordian section to permit flexing, extension or contraction of said applicator tip.

23. The applicator according to claim 1, wherein at least one of said container body and said applicator tip has at least one male mating feature and the other of said container body and said applicator tip has at least one complementary female mating feature for attaching said applicator tip to said container body.

24. The applicator according to claim 1, wherein said adhesive material is a synthetic or semi-synthetic polymerizable or cross-linkable monomer material.

25. The applicator according to claim 1, wherein said porous material has a polymerization or cross-linking initiator or rate modifier for said adhesive material disposed thereon or therein.

26. The applicator according to claim 1, wherein said adhesive material comprises 1,1-disubstituted ethylene monomers.

27. The applicator according to claim 1, wherein said adhesive material comprises α-cyanoacrylate monomers.

28. A method of applying an adhesive material to a substrate using the applicator of claim 1, comprising forcing said adhesive material from said container body through said applicator tip onto said substrate.

29. The method according to claim 28, wherein said substrate is tissue.

* * * * *